(12) United States Patent
Bauerfeind (10) Patent No.: US 10,383,400 B2
(45) Date of Patent: Aug. 20, 2019

(54) VISCO-ELASTIC INSERT

(71) Applicant: Bauerfeind AG, Zeulenroda-Triebes (DE)

(72) Inventor: Thomas Bauerfeind, Krefeld (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 337 days.

(21) Appl. No.: 15/137,914

(22) Filed: Apr. 25, 2016

(65) Prior Publication Data

US 2016/0235159 A1 Aug. 18, 2016

Related U.S. Application Data

(63) Continuation of application No. PCT/EP2014/072689, filed on Oct. 22, 2014.

(30) Foreign Application Priority Data

Oct. 25, 2013 (DE) .................. 10 2013 018 265

(51) Int. Cl.
| | | |
|---|---|---|
| *A43B 17/00* | (2006.01) | |
| *A43B 17/02* | (2006.01) | |
| *A43B 7/16* | (2006.01) | |
| *A43B 7/14* | (2006.01) | |
| *A43B 13/18* | (2006.01) | |
| *A43B 17/16* | (2006.01) | |
| *A43B 21/32* | (2006.01) | |
| *A61F 5/14* | (2006.01) | |

(52) U.S. Cl.
CPC ............ *A43B 17/003* (2013.01); *A43B 7/144* (2013.01); *A43B 7/148* (2013.01); *A43B 7/16* (2013.01); *A43B 13/186* (2013.01); *A43B 13/188* (2013.01); *A43B 17/023* (2013.01); *A43B 17/16* (2013.01); *A43B 21/32* (2013.01); *A61F 5/14* (2013.01)

(58) Field of Classification Search
CPC ........... A43B 7/144; A43B 7/148; A43B 7/16; A43B 13/186; A43B 13/188; A43B 17/16; A43B 17/003; A43B 17/023
See application file for complete search history.

(56) References Cited

U.S. PATENT DOCUMENTS

| | | | | |
|---|---|---|---|---|
| 2,046,732 A | * | 7/1936 | Fein ....................... | A43B 17/18 36/43 |
| 3,859,740 A | * | 1/1975 | Kemp ................... | A43B 21/32 36/71 |

(Continued)

FOREIGN PATENT DOCUMENTS

| | | |
|---|---|---|
| DE | 295 04 057 U1 | 4/1995 |
| DE | 298 06 187 U1 | 7/1999 |

OTHER PUBLICATIONS

International Search Report dated Mar. 6, 2015 of international application PCT/EP2014/072689 on which this application is based.

(Continued)

*Primary Examiner* — Jila M Mohandesi
(74) *Attorney, Agent, or Firm* — Ewers & Hasselmann PLLC (57) ABSTRACT

The present invention relates to visco-elastic inserts, in particular to shoe inserts, and in particular to heel supports having a main body with regions of dissimilar hardness.

5 Claims, 6 Drawing Sheets

(56) References Cited

U.S. PATENT DOCUMENTS

| | | | |
|---|---|---|---|
| 4,530,173 A * | 7/1985 | Jesinsky, Jr. | A43B 21/32 36/173 |
| 4,928,404 A | 5/1990 | Scheuermann | |
| 6,061,929 A * | 5/2000 | Ritter | A43B 3/0052 36/107 |
| 6,460,275 B1 * | 10/2002 | Bennett | A61F 5/14 36/144 |
| 8,997,379 B2 | 4/2015 | Reinhardt et al. | |
| 2001/0039746 A1 * | 11/2001 | Seiter | A43B 7/142 36/44 |
| 2002/0050080 A1 * | 5/2002 | Vasyli | A43B 7/141 36/145 |
| 2002/0092203 A1 * | 7/2002 | Hardt | A43B 7/142 36/43 |
| 2003/0070321 A1 * | 4/2003 | Davis | A43B 7/144 36/43 |
| 2004/0118017 A1 * | 6/2004 | Dalton | A43B 7/142 36/44 |
| 2006/0185197 A1 * | 8/2006 | Rhenter | A43B 1/0045 36/174 |
| 2007/0180632 A1 * | 8/2007 | Gallegos | A43B 1/0054 12/146 B |
| 2008/0271340 A1 * | 11/2008 | Grisoni | A43B 7/142 36/43 |
| 2010/0212187 A1 * | 8/2010 | Jones | A43B 3/0047 36/44 |
| 2012/0017467 A1 * | 1/2012 | Whitney | A43B 3/0031 36/31 |
| 2013/0081306 A1 * | 4/2013 | Park | A43B 7/1425 36/43 |

OTHER PUBLICATIONS

Translation of international preliminary report on patentability dated Feb. 15, 2016 of international application PCT/EP2014/072689 on which this application is based.

* cited by examiner

VISCO-ELASTIC INSERT

CROSS REFERENCE TO RELATED APPLICATIONS

This application is a continuation application of international patent application PCT/EP2014/072689, filed Oct. 22, 2014, designating the United States and claiming priority from German application 10 2013 018 265.4, filed Oct. 25, 2013, and the entire content of both applications is incorporated herein by reference.

FIELD OF THE INVENTION

The present invention relates to visco-elastic inserts, in particular to shoe inserts, and in particular to heel inserts, having a main body with regions of dissimilar hardness.

BACKGROUND OF THE INVENTION

Inserts, in particular shoe inserts, and in particular heel inserts, are known in various embodiments. Providing a foot with an insert, for example, providing a hind foot with a heel support, serves for compensating differences in the length of legs, for damping one's tread, for absorbing shock peaks, for positively influencing the posture and gait patterns, and the like. Heel supports from silicone-based rubber have been particularly successful because this material cannot be configured so as to be compressible but nevertheless can be configured so as to be resilient/elastic. Silicone-based rubbers in terms of the resilience thereof relating to the respectively set requirements may be readily specified and are also easy to shape.

Conventional visco-elastic inserts, in particular heel inserts, are composed of silicone-based rubber of the same material specification. The distribution of pressure on the foot and in particular on the hind foot may be largely homogenized in this way. However, most often the pressure is higher in the region of the heel spur on the plantar fascia. This may have a negative effect, in particular in the case of malpositioning of the heel or of the heel spur. Accordingly, U.S. Pat. No. 4,928,404 proposed a heel cushion from silicone-based rubber, with a heel bed having a punctiform region which is composed of a silicone-based rubber of softer specification. This soft region is disposed such that it is located below the heel spur, the compressive stress of the hind foot below the heel spur thus being reduced. However, it is disadvantageous in the case of such a punctiform region that a perceptible edge which may cause pain exists between the shore hardness of a spot and of the main body. This is also the case in an embodiment in which the soft region is enlarged, since the respective contours of the sole of the foot cannot be bordered, stabilized, and guided in an anatomically correct manner, potentially enabling the foot to sink into the soft foot bed, which may result in further pain or instability.

SUMMARY OF THE INVENTION

A technical problem on which the present invention is based is that of providing an insert which overcomes the disadvantages of the prior art. In particular, a technical problem on which the present invention is based is that of providing inserts, and in particular heel wedges, which not only relieve the appendix of the heel spur but at the same time enable a hollow support in the entire profile of the plantar fascia.

The technical problem is solved by a heel support including: a main body including a first region made from a first visco-elastic material with a first hardness, a second region made from a second visco-elastic material with a second hardness, and a third region made from a third visco-elastic material with a third hardness; and, a shell arranged on an outer edge of the main body; the second region being surrounded by the first region and the third region being surrounded by the second region; the second visco-elastic material of the second region being softer than the first visco-elastic material of the first region; the third visco-elastic material of the third region being softer than the second visco-elastic material of second region; the first region having a first abutting edge, the second region having second inner and outer abutting edges, and the third region having a third abutting edge; the first abutting edge, the second inner and outer abutting edges, and the third abutting edge having protrusions and abutting clearances; the first abutting edge of the first region and the second outer abutting edge of the second region being intermeshed with each other through the protrusions and abutting clearances of the first abutting edge and the second outer abutting edge in a mutually matching serpentine manner or in a toothed manner; the second inner abutting edge of the second region and the third abutting edge of the third region being intermeshed with each other through the protrusions and abutting clearances of the second inner abutting edge and the third abutting edge in a mutually matching serpentine manner or in a toothed manner; and, the second region having a kidney-like or a tear-like planar shape.

In particular, the present invention achieves the solution to the technical problem by providing a heel support including a main body with a first region with a first hardness. The main body has a second region with a second hardness. The second region with the second hardness is softer than the first region with the first hardness and is surrounded by the first region with the first hardness. The main body has a third region with a third hardness. The third region with the third hardness is softer than the second region with the second hardness and is surrounded by the second region with the second hardness.

A heel spur which is located on the plantar fascia, that is, on an aponeurosis in the region of the sole of the foot, is formed on the tendon replacement of muscles on the heel bone as a consequence of microinjuries to the tissue, which may arise by overstraining, for example. In the course of healing these microinjuries, as a repair measure the body deposits bone material in the ankle tendon. Inflammations, referred to as plantar fasciitis, may arise should there be any irritation in the region of the ossified ankle tendon. In turn, inflammations may lead to fortified ossification and thus to permanent deterioration, bearing the risk of a chronic profile.

Surprisingly, it has been demonstrated that a configuration according to an aspect of the invention, and in particular of a heel support having three different regions of dissimilar hardness, that is, having a second intermediate region which is softer than the first main region but is harder than the punctiform region on the heel spur, by way of interaction between the second region and the third region, both acting in a proprioceptive manner, advantageously leads to a particularly positive therapeutic effectiveness in the presence of a heel spur and particularly well reduces the symptoms caused by the heel spur. A synergetic effect is achieved in that not only the heel spur is relieved by the third particularly soft region on which the heel spur is bedded when the insert is being worn, and the second somewhat harder region which guides the foot, but at the same time the entire profile of the plantar fascia is relieved or may even be supported in a hollow manner, respectively.

The inserts according to an aspect of the invention are particularly suitable in the case of sole pains, particularly in the case of compressive plantar pain. The inserts according to an aspect of the invention may be used, for example, in the case of pain which is caused by a heel spur, or else by arthrosis in the sole region. Further aspects of application include achillodynia, Haglund's deformity, a difference in the length of legs, and further types of hind foot symptoms.

According to an aspect of the invention, the insert has a shell which adjoins the periphery of the first region of the main body.

The shell which preferably adjoins the periphery of the first region of the main body serves in particular as a peripheral elevation in the rear region of the insert, in particular of the heel support.

According to an aspect of the invention, the insert, or the heel support, respectively, having a shell arranged on an edge or periphery of the first region of the main body advantageously leads to further synergetic interaction between the three elements of the third soft main-body region, the second harder main-body region, and the shell which adjoins the first region of the main body and serves as a peripheral elevation in the rear region. The combination of these three features leads to an effective mechanism which is created by the bedding of the foot by the soft third region and by simultaneously providing guiding by the somewhat harder second region. Evasive movement is prevented by the shell which encloses the hind foot. By combining these three features, there results a holistic system in which not only the heel spur is relieved and the entire profile of the plantar fascia is relieved, or may even be supported in a hollow manner, respectively, but in which at the same time the hind foot is stabilized by the shell. Medial support on the calcaneus also acts in this sense. In a synergetic manner, the three elements reduce the pronation movement of the hind foot and, on account thereof, reduce the tensile load on the plantar fascia. By way of this combination of the elements of a soft third region, a harder second region, and a shell serving as a peripheral elevation on the first region, the insert, in particular the heel support, is suitable for simultaneously positively influencing the symptom profile of plantar fasciitis at various levels.

According to an aspect of the invention, the first region of the main body and the adjoining shell are made from the same material.

According to another aspect of the invention, the main body is made from at least one visco-elastic material, preferably from one visco-elastic material, or from a material that predominantly contains visco-elastic materials.

According to a further aspect of the invention, the first region is made from a first visco-elastic material with a first hardness, the second region is made from a second visco-elastic material with a second hardness, and the third region is made from a third visco-elastic material with a third hardness.

According to an aspect of the present invention, the first material has a hardness of 45 to 60 Shore. According to another aspect of the invention, the second material has a hardness of 25 to 50 Shore, preferably of 35 to 50 Shore. According to yet another aspect of the invention, the third material has a hardness of 20 to 30 Shore. According to another aspect of the invention, the first material has a hardness of 45 to 60 Shore, the second material has a hardness of 25 to 50 Shore, preferably of 35 to 50 Shore, and the third material has a hardness of 20 to 30 Shore.

According to a further aspect of the invention, the first region is made from a first visco-elastic material with a first hardness, and the third region is made from a second visco-elastic material with a second hardness. The second region is made from elements of the second visco-elastic material that are embedded in the first visco-elastic material. According to an aspect of the invention, the first material has a hardness of 45 to 60 Shore, and the second material has a hardness of 20 to 30 Shore.

The hardness of the second region may be specified by the number and size of the elements from the second visco-elastic material that are embedded in the first visco-elastic material. The elements may be of any shape.

According to a further aspect of the invention, the first region is made from a first visco-elastic material with a first hardness, and the third region is made from a second visco-elastic material with a second hardness. The second region is made from elements of the first visco-elastic material that are embedded in the second visco-elastic material. According to an aspect of the present invention, the first material has a hardness of 45 to 60 Shore, and the second material has a hardness of 20 to 30 Shore.

The hardness of the second region may be specified by the number and size of the elements from the first visco-elastic material that are embedded in the second visco-elastic material. The elements may be of any shape.

The respective material of the first region, of the second region, and of the third region may be the same visco-elastic basic material, for example silicone, in particular silicone rubber, which in the respective region is specified to the respective hardness. A person skilled in the art is conversant with the manner in which suitable materials may be specified to a certain hardness, in particular during the manufacture of the insert.

Of course, it may alternatively also be provided that the second region and/or the third region of the main body are/is composed of another material than the first region.

The main body of the insert may be composed of rubber, silicone, preferably silicone-based rubber, of a soft elastic or of a thermoplastic elastomer.

The insert may predominantly contain rubber, silicone, preferably silicone-based rubber, a soft elastic or a thermoplastic elastomer.

The insert may contain rubber, silicone, preferably silicone-based rubber, a soft elastic or a thermoplastic elastomer.

The insert may be composed of silicone. In particular, the insert may be composed of silicone-based rubber.

According to an aspect of the invention, the area of the second region with the second hardness, together with the area of the third region with the third hardness, accounts for at least half the area of the main body of the insert or of the heel support.

The second and the third region of the main body are located in the heel region of the insert.

Depending on the prevailing circumstances, the third region may be disposed on the insert so as to be centric or eccentric.

The main body of the insert forms a base area which faces the foot, on which at least a part of a sole of a foot may bear. The insert may be composed either of only the main body or of the main body and the peripherally adjoining shell. Suitable shapes of such inserts with or without a shell on the peripheral side are known to a person skilled in the art.

According to an aspect of the invention, the abutting edges of the first region and of the second region are intermeshed. According to another aspect of the invention, the abutting edges of the first region and of the second region are intermeshed by way of protrusions and matching clearances in a mutually matching serpentine manner or toothed manner or in any other manner.

According to an aspect of the invention, the abutting edges of the second region and of the third region are intermeshed. According to another aspect of the invention, the abutting edges of the second region and of the third region are intermeshed by way of protrusions and matching clearances in a mutually matching serpentine manner or toothed manner or in any other manner.

The intermeshing of the first region and the second region and/or of the second region and the third region has the unexpected technical advantage that in the boundary region between the regions, part-regions with one hardness engage in part-regions with another hardness. On account thereof, a transitional portion results which is not perceived to be excessively hard. Moreover, intermeshing according to an aspect of the invention enables the interfaces in the transitional region between the first and the second region and/or between the second and the third region to be enlarged. Enlargement of the interface of a contact portion advantageously leads to the two mutually bearing regions having improved mutual bonding.

According to yet another aspect of the invention, the second region with a second hardness has a round, oval, stellar, kidney-like, oak-leaf like, or tear-like planar shape. However, the second region may also have another basic shape.

The insert may be a shoe insert, in particular an orthopedic shoe insert, a heel support, or an insert sole, in particular a sports insert sole.

According to an aspect of the invention, the insert is a heel support, also referred to as a heel cushion. The heel support according to the aspect of the invention is wedge-shaped, that is, is a heel wedge.

The thickness of the main body tapers off toward the front.

The heel support, in particular the heel wedge, may be configured as a pronation support having an external elevation, or as a supination support having an internal elevation.

According to an aspect of the invention, the shell does not adjoin the periphery of the main body that points to the front.

The first material with a first hardness, the second material with a second hardness, and the third material with a third hardness are made of silicone-based rubber.

In the context of the present invention, "the second region is surrounded by the first main-body region" and "the third region is surrounded by the second main-body region" is understood to mean that the first region at least partially delimits the second region, and that the second region at least partially delimits the third region. The second region may but need not be upwardly and/or downwardly delimited by the first region, and the third region may but need not be upwardly and/or downwardly delimited by the second region. The third region may but need not be upwardly and/or downwardly delimited by the first region.

According to an aspect of the invention, the second region that is made from a second visco-elastic material with a second hardness, and the third region that is made from a third visco-elastic material with a third hardness are coated with the first visco-elastic material with the first hardness on the surface that points toward the sole of the foot.

According to another aspect of the invention, the second region that is made from a second visco-elastic material with a second hardness, and the third region that is made from a third visco-elastic material with a third hardness are integrally cast in the first visco-elastic material with a first hardness.

In terms of manufacturing technology, it is particularly preferable for the lower side of the insert to be continuously composed of silicone-based rubber with the hardness of the first region, and for the second region and for the third region to be composed of silicone-based rubber which is specified to be softer and to be embedded in the silicone-based rubber with the hardness of the first region.

BRIEF DESCRIPTION OF THE DRAWINGS

The invention will now be described with reference to the drawings wherein.

DESCRIPTION OF THE PREFERRED EMBODIMENTS OF THE INVENTION

Figure 1A:
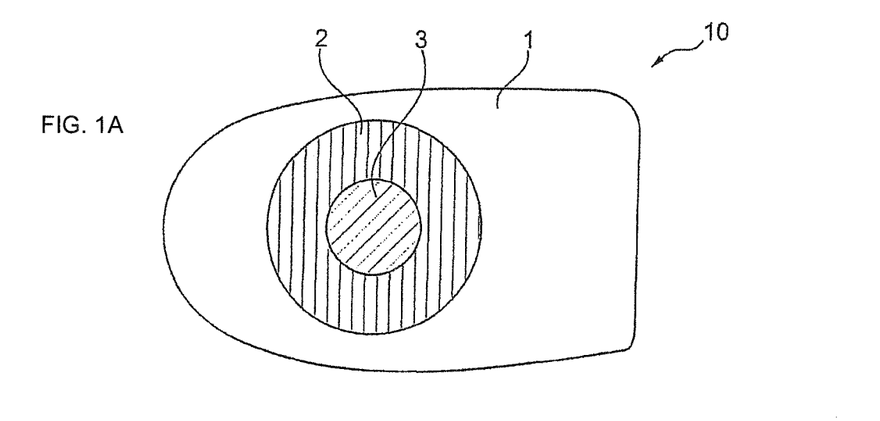
FIGS. 1A to 1C show a heel support according to example embodiments of the invention.

FIG. 1A shows a plan view of an insert according to an example embodiment of the invention, in the form of a heel support 10, having a visco-elastic main body which has a first region 1, a second region 2, and a third region 3. The first region 1 is composed of a visco-elastic material, for example of silicone-based rubber, with a hardness of 45 to 60 Shore. The second region 2 is softer than the main-body region 1 with the first hardness, and is surrounded by the first main-body region 1. The second region 2 is composed of a visco-elastic material, for example of silicone-based rubber, with a hardness of 25 to 50 Shore, preferably of 35 to 50 Shore. The third region 3 is softer than the second main-body region 2 with the second hardness, and is surrounded by the second main-body region 2. The third region 3 is composed of a visco-elastic material, for example of silicone-based rubber, with a hardness of 20 to 30 Shore.

The configuration of the insert shown in FIG. 1A has the advantage that a heel spur may be relieved by the third soft region 3, the somewhat harder second region 2 at the same time having a hardness and a size which allow for the foot to be guided and for the entire profile of the plantar fascia to be relieved.

The transition from the soft third region 3 via the somewhat harder second region 2 to the hardest first region 1 has the further advantage that a positive wearing sensation is created when the visco-elastic insert 10 is treaded on, and that no edges between a soft region and a harder main region are perceptible.

Figure 1B:
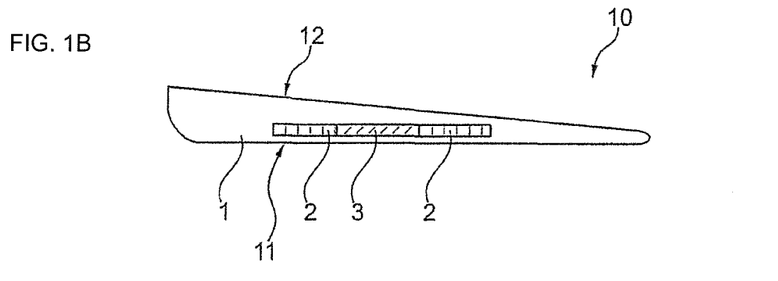

FIG. 1B is a cross-section view of the heel support in the form of a heel wedge 10 shown in FIG. 1A according to an example embodiment of the invention. The heel wedge has a visco-elastic main body which has a first region 1, a second region 2, and a third region 3. The second region 2 and the third region 3 are surrounded by the material of the first region 1, or are integrally cast in the material of the first region 1, respectively, both at the top, that is, in the direction of the foot bed 12, as well as on the bottom, that is, in the direction of the lower face 11.

Figure 1C:
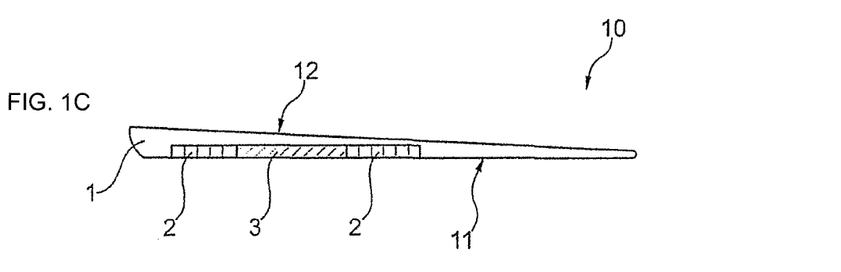

FIG. 1C is a cross-section view of the heel support shown in FIG. 1A in the form of a heel wedge 10 according to an example embodiment. The heel wedge has a visco-elastic main body which has a first region 1, a second region 2, and a third region 3. The second region 2 and the third region 3 are surrounded by the material of the first region 1 or are integrally cast in the material of the first region 1, respectively, only at the top, that is, in the direction of the foot bed 12. In the downward direction the second region 2 as well as the third region 3 reach down to the lower face 11.

Figure 2A:
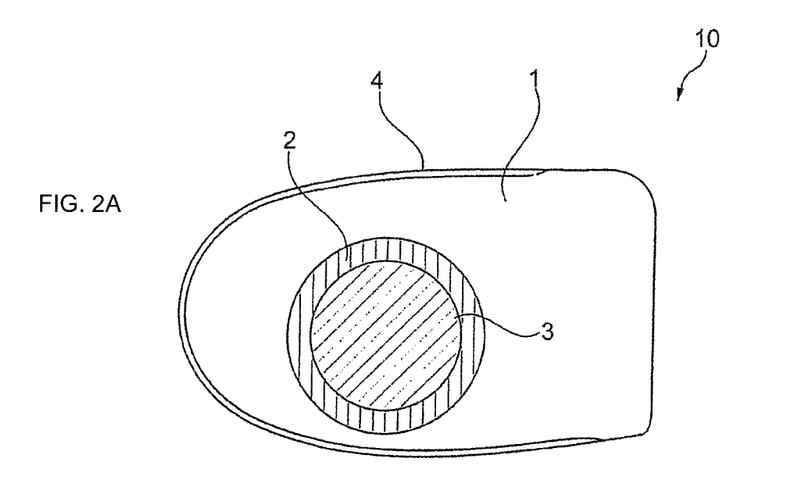
FIGS. 2A and 2B show a heel support having a shell according to an example embodiment of the invention.

FIG. 2A is a plan view of the heel support 10 of FIG. 1A having a visco-elastic main body which has a first region 1, a second region 2, and a third region 3. A shell 4 is located on the lateral and rear periphery of the first region 1.

Figure 2B:
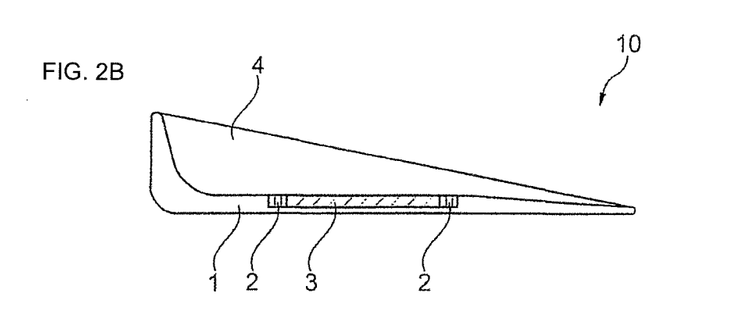

FIG. 2B is a cross-section view of the heel support of FIG. 2A with the first region 1, the second region 2, and the third region 3. The shell 4 tapers off from the rear to the front along the main body.

In combination with the soft third region 3 and the somewhat harder second region 2, the additional shell 4 has the effect that an evasive movement by the shell 4 which encloses the hind foot is prevented. This results in a holistic system in which not only the heel spur is relieved and the entire profile of the plantar fascia is relieved, or may even be supported in a hollow manner, respectively, but in which at the same time the hind foot is stabilized by the shell 4.

Figure 3A:
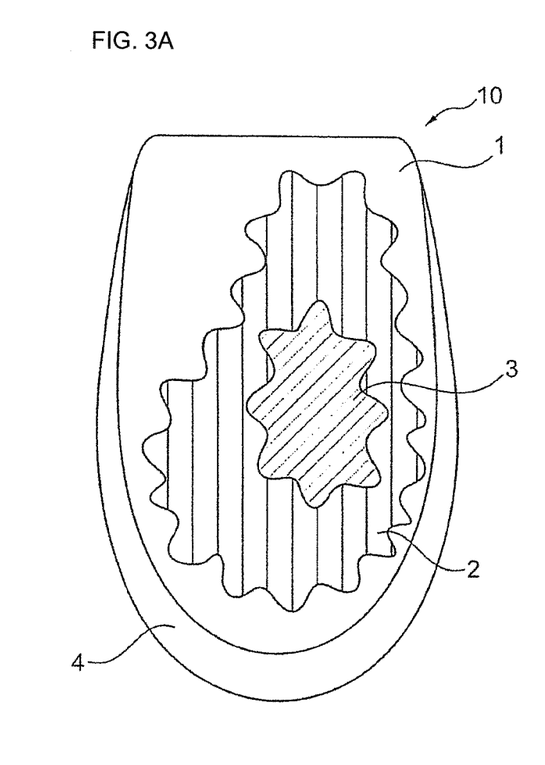
FIGS. 3A and 3B show a heel support for a left foot and for a right foot according to an example embodiment of the invention.

FIG. 3A is a plan view of a heel support 10 for a left foot according to an example embodiment of the invention with a first region 1, a second region 2, and a third region 3, as well as a shell 4. The basic shape of the second region 2 is kidney-like; the basic shape of the third region 3 is oval. The second region 2 and the third region 3 occupy more than half the base area of the heel support 10.

The shape of the second region 2, and the large area of the total area composed of the second region 2 and of the third region 3 lead to a particularly positive wearing sensation and to the entire plantar fascia being able to be relieved in a particularly positive manner.

The first region 1 and the second region 2 are intermeshed. The second region 2 and the third region 3 are also intermeshed. Apart from aesthetic aspects, such intermeshing has the technical advantage that it results in a transitional region which has a shore hardness which is between the shore hardnesses of the adjacent regions. As a result, the transitional regions are not perceived to be that hard. The interfaces in the transitional portion between the respectively adjacent regions 1 and 2, or 2 and 3, respectively, are also increased such that the visco-elastic materials of the mutually adjacent regions have improved mutual bonding.

Figure 3B:
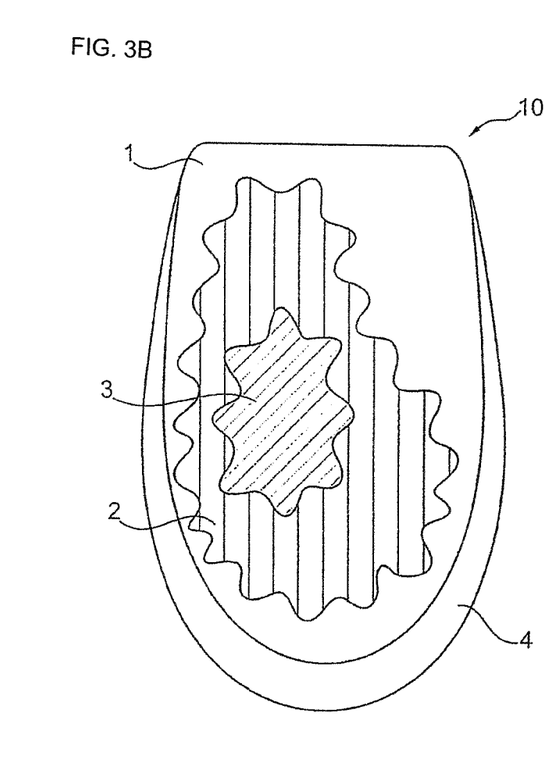

FIG. 3B is a plan view of the heel support 10 of FIG. 3A, for a right foot with a first region 1, a second region 2, and a third region 3, as well as a shell 4.

Figure 4A:
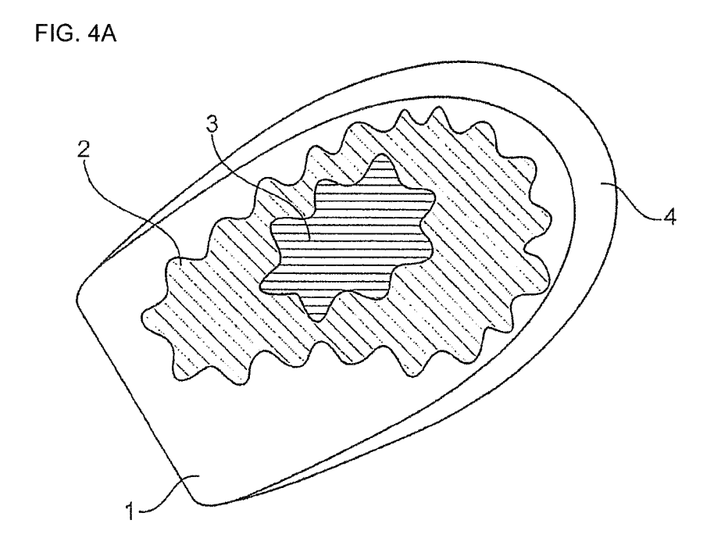
FIGS. 4A and 4B show a plan view and a cross-sectional view of the heel support of FIG. 3A according to an example embodiment of the invention.

FIG. 4A is a cross-section view of the heel support 10 of FIG. 3A with a first region 1, a second region 2, and a third region 3, as well as a shell 4. The shell 4 tapers off from the rear to the front along the main body.

Figure 4B:
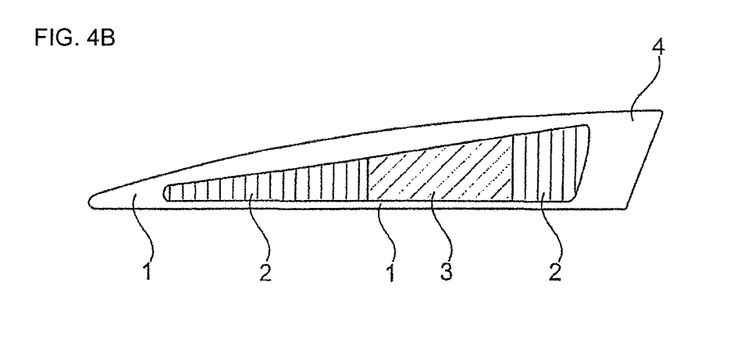

FIG. 4B is a cross section of the heel support 10 of FIG. 3A with a first region 1, a second region 2, and a third region 3, as well as a shell 4. The shell 4 tapers off from the rear to the front along the main body.

Figure 5A:
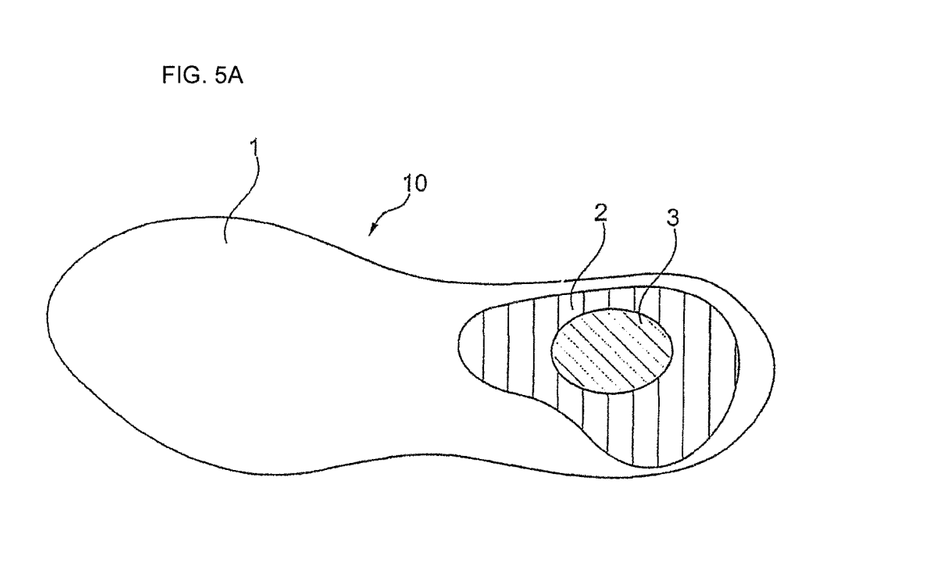
FIGS. 5A and 5B show an insert and a heel support according to example embodiments of the invention.

FIG. 5A is a plan view of an insert 10 according to an example embodiment of the invention, for a left foot with a first region 1, a second region 2, and a third region 3. The basic shape of the second region 2 is kidney-like; the basic shape of the third region 3 is oval. The second region 2 and the third region 3 occupy more than half the base area of the heel area of the insert 10.

Figure 5B:
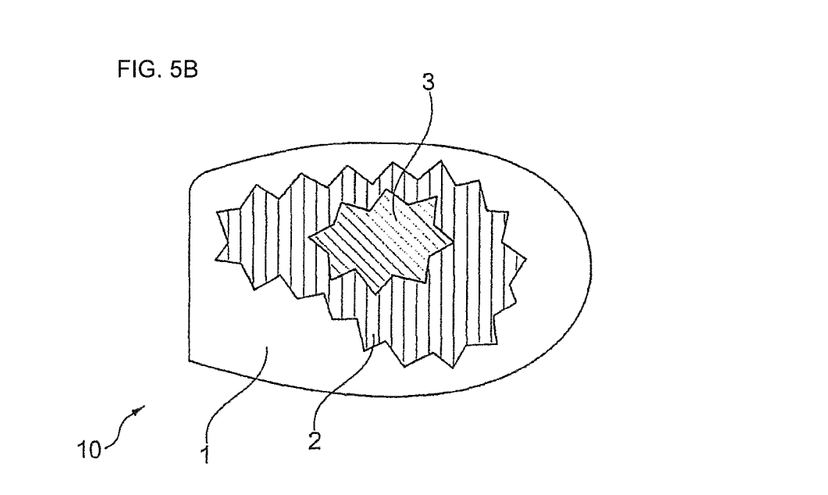

FIG. 5B is a plan view of a heel support 10 according to a further example embodiment of the invention with a first region 1, a second region 2, and a third region 3. The basic shape of the second region 2 is kidney-like; the basic shape of the third region 3 is oval. The second region 2 and the third region 3 occupy more than half the base area of the heel support 10. The first region 1 and the second region 2 are intermeshed by way of teeth. The second region 2 and the third region 3 are also intermeshed by teeth.

Figure 6A:
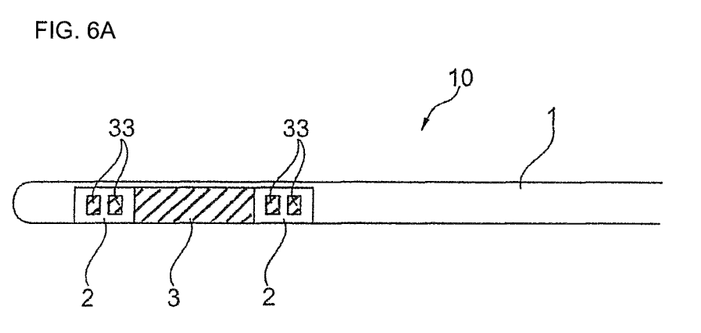
FIGS. 6A and 6B show an insert in a plan view and in a cross section view according to an example embodiment of the invention.

FIG. 6A is a cross section of an insert 10 according to an example embodiment of the invention, having a visco-elastic main body which has a first region 1 and a third region 3. The first region 1 is composed of a visco-elastic material, for example of silicone-based rubber, with a hardness of 45 to 60 Shore. The third region 3 is composed of a visco-elastic material, for example of a silicone-based rubber, with a hardness of 20 to 30 Shore. The third region 3 is surrounded by a second region 2. The second region 2 is made from the harder material of the first region 1, and elements 33 embedded therein are made from the softer material of the third region 3. On account thereof, the second region 2 is also visco-elastic, having a hardness of 25 to 50 Shore, preferably of 35 to 50 Shore. The elements 33 are cylindrical. However, the latter may also have any other suitable shape; they may be spherical, rod-shaped, or hexahedron-shaped, for example.

Alternatively, the second region 2 may also be made in that elements from the harder material of the first region 1 are embedded in the softer material of the third region 3.

Figure 6B:
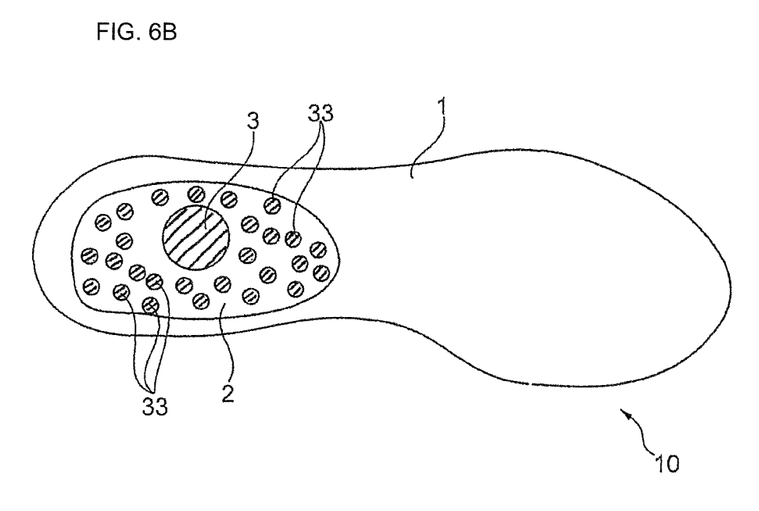

FIG. 6B is a plan view of insert 10 of FIG. 6A according to an example embodiment of the invention, having a visco-elastic main body which has a first region 1 and a third region 3. The second region 2 is made from the harder material of the first region 1 and from elements 33 from the softer material of the third region 3, which are embedded therein.

In summary, an insert 10 is provided which has a main body with a first region 1 with a first hardness. The main body has a second region 2 with a second hardness. The second region with the second hardness is softer than the first region with the first hardness and is surrounded by the first region with the first hardness. The insert 10 has a shell 4 which adjoins the periphery of the first region 1 of the main body. The main body has a third region 3 with a third hardness. The third region with the third hardness is softer than the second region 2 with the second hardness and is surrounded by the second region 2 with the second hardness. The abutting edges of the first region 1 and of the second region 2 are intermeshed by way of protrusions and matching clearances in a mutually matching serpentine manner or toothed manner. The abutting edges of the second region 2 and of the third region 3 are intermeshed by way of protrusions and matching clearances in a mutually matching serpentine manner or toothed manner. The second region 2 has a kidney-like or tear-like planar shape, and either the first region 1 is formed from a first visco-elastic material with a first hardness, the second region 2 is formed from a second visco-elastic material with a second hardness, and the third region 3 is formed from a third visco-elastic material with a third hardness, or the first region 1 is formed from a first visco-elastic material with a first hardness, and the third region 3 is formed from a second visco-elastic material with a second hardness, and the second region 2 is formed from elements 33 of the second visco-elastic material that are embedded in the first visco-elastic material. The insert 10 is a heel support or heel cushion.

It is understood that the foregoing description is that of the example embodiments of the invention and that various changes and modifications may be made thereto without departing from the spirit and scope of the invention as defined in the appended claims.

What is claimed is:

1. A heel support comprising:

a main body including a foot bed surface pointing toward a sole of a foot, a floor surface, a first region made from a first visco-elastic material with a first hardness, a second region defining a first portion of the floor surface and being made from a second visco-elastic material with a second hardness, a third region defining a second portion of the floor surface and being made from a third visco-elastic material with a third hardness, and a layer provided between the foot bed surface and the second and third regions; and, a shell arranged on an outer edge of said main body and being made from the first visco-elastic material;

said layer being made from the first visco-elastic material;

said second region being surrounded by said first region and said third region being surrounded by said second region;

said second visco-elastic material of said second region being softer than said first visco-elastic material of said first region;

said third visco-elastic material of said third region being softer than said second visco-elastic material of second region;

said first region having a first abutting edge, said second region having second inner and outer abutting edges, and said third region having a third abutting edge;

said first abutting edge, said second inner and outer abutting edges, and said third abutting edge having protrusions and abutting clearances;

said first abutting edge of said first region and said second outer abutting edge of said second region being intermeshed with each other through the protrusions and abutting clearances of said first abutting edge and said second outer abutting edge in a mutually matching serpentine manner;

said second inner abutting edge of said second region and said third abutting edge of said third region being intermeshed with each other through the protrusions and abutting clearances of said second inner abutting edge and said third abutting edge in a mutually matching serpentine manner; and, said second region having a kidney like or a tear like planar shape, wherein a thickness of the main body tapers off toward a front area of the main body thereby forming a front edge of the main body, and wherein the shell does not extend to the front edge of the main body.

2. The heel support of claim 1, wherein:

said first visco-elastic material has a hardness of 45 to 60 Shore, said second visco-elastic material has a hardness of 25 to 50 Shore, and said third visco-elastic material has a hardness of 20 to 30 Shore.

3. The heel support of claim 1, wherein the first visco-elastic material with the first hardness, the second first visco-elastic material with the second hardness, and the third first visco-elastic material with the third hardness are silicone based rubber materials.

4. The heel support of claim 1, wherein the second region that is made from the second visco-elastic material with the second hardness and the third region that is made from the third visco-elastic material with the third hardness are integrally cast in the first visco-elastic material with the first hardness.

5. The heel support of claim 1, wherein the second region has an oak-leaf like shape.

* * * * *